United States Patent [19]
Karim et al.

[11] Patent Number: 6,114,278
[45] Date of Patent: Sep. 5, 2000

[54] CATALYSTS FOR CATALYTIC OXIDATION OF PROPANE TO ACRYLIC ACID, METHODS OF MAKING AND USING THE SAME

[75] Inventors: Khalid Karim, Manchester, United Kingdom; Yajnavalkya Subrai Bhat, Riyadh, Saudi Arabia; Syed Irshad Zaheer, Riyadh, Saudi Arabia; Abdullah Bin Nafisah, Riyadh, Saudi Arabia

[73] Assignee: Saudi Basic Industries Corporation, Saudi Arabia

[21] Appl. No.: 09/193,015

[22] Filed: Nov. 16, 1998

[51] Int. Cl.⁷ .................................................. B01J 23/00
[52] U.S. Cl. ................ 502/312; 502/240; 502/246; 502/247; 502/248; 502/254; 502/255; 502/257; 502/261; 502/262; 502/303; 502/305; 502/306; 502/307; 502/308; 502/311
[58] Field of Search ............................... 502/240, 246, 502/247, 248, 254, 255, 257, 261, 262, 305, 303, 306, 307, 308, 311, 312

[56] References Cited

U.S. PATENT DOCUMENTS

| | | | |
|---|---|---|---|
| 4,049,583 | 9/1977 | Lauder | 423/594 |
| 4,110,254 | 8/1978 | Lauder | 423/213.5 |
| 4,182,694 | 1/1980 | Lauder | 423/213.5 |
| 5,198,580 | 3/1993 | Bartek et al. | 562/542 |
| 5,470,815 | 11/1995 | Kim et al. | 502/311 |

FOREIGN PATENT DOCUMENTS

| | | |
|---|---|---|
| 0 608 838 A2 | 3/1994 | European Pat. Off. |
| 0 608 838 A3 | 3/1994 | European Pat. Off. |

OTHER PUBLICATIONS

Jpn. Kokai Koho JP 10 45,643; Ushikubo, Takashi, "Preparation of Acrolein and Acrylic Acid by Catalytic Oxidation of Propane . . . ", Chemical Abstract No. 128:204621z, Feb. 17, 1998.

*Primary Examiner*—Elizabeth Wood
*Attorney, Agent, or Firm*—Whitman Breed Abbott & Morgan LLP

[57] ABSTRACT

A mixed metal oxide Mo-V-Ga-Pd-Nb-X (where X=La, Te, Ge, Zn, Si, In or W) catalytic system providing a higher selectivity to acrylic acid in the low temperature partial oxidation of propane with a molecular oxygen-containing gas.

29 Claims, 2 Drawing Sheets

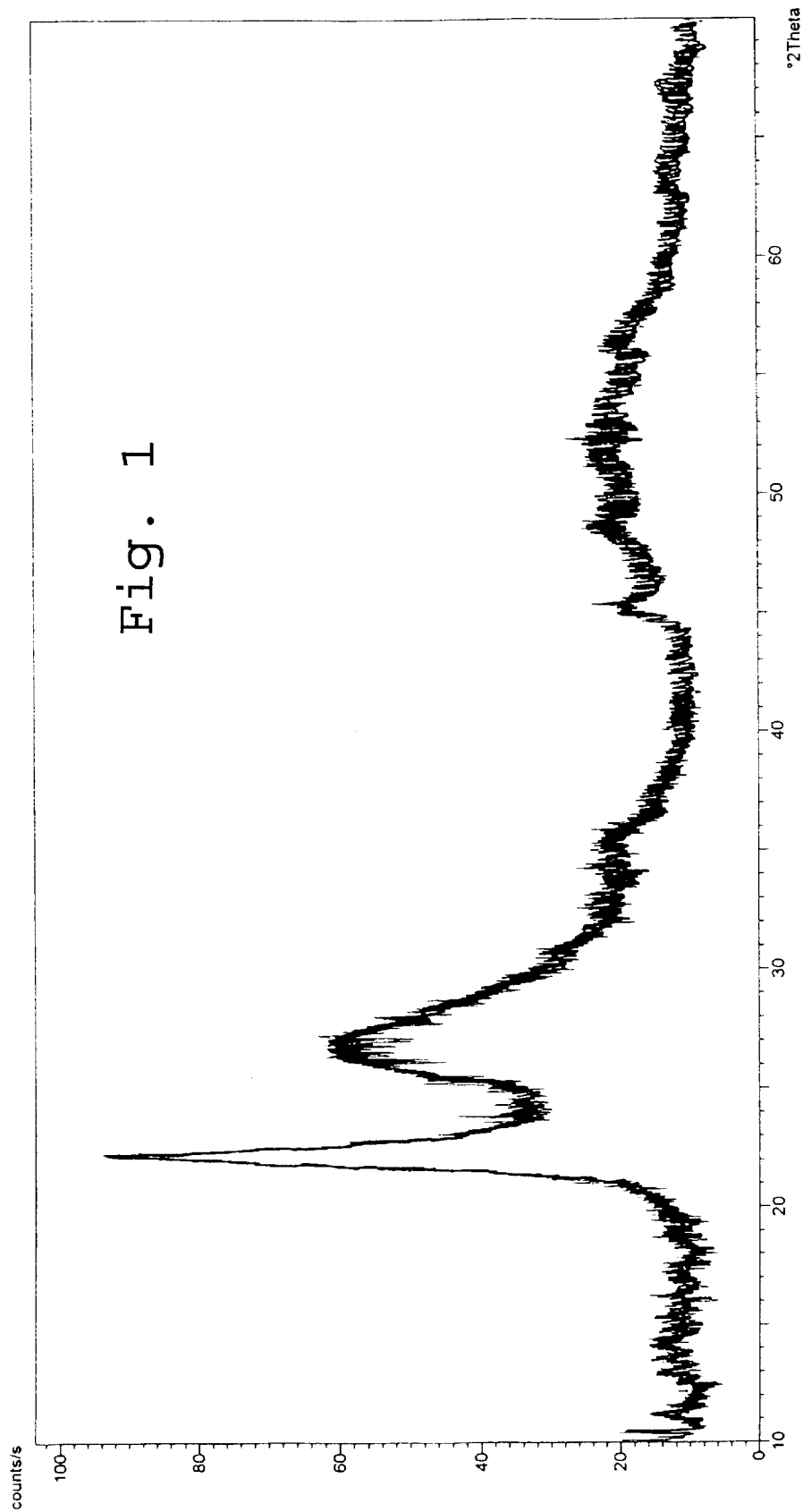

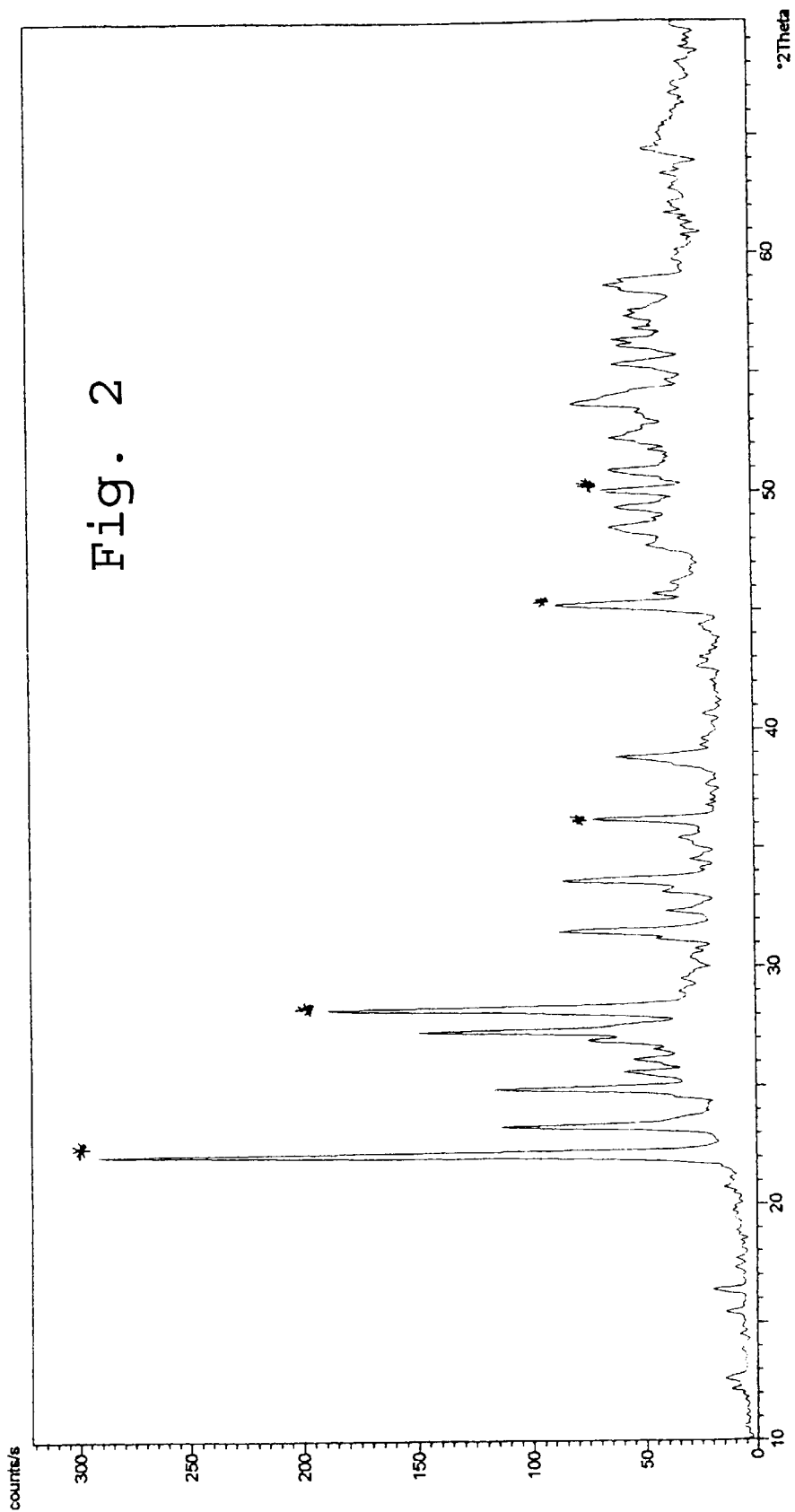

CATALYSTS FOR CATALYTIC OXIDATION OF PROPANE TO ACRYLIC ACID, METHODS OF MAKING AND USING THE SAME

BACKGROUND OF THE INVENTION

1. Field of Invention

A novel mixed metal oxide catalyst for the production of acrylic acid through catalytic vapor phase partial oxidation of propane and its use for one stage selective production of acrylic acid and acrolein at lower temperatures.

2. Description of Related Art

Several publications are referenced in this application. These references describe the state of the art to which this invention pertains and are hereby incorporated by reference.

The two stage vapor phase oxidation of propylene for the production of acrylic acid is known to the art. However, there is no commercial process that exists based on propane oxidation to acrylic acid. The production of acrylic acid from propane would be more attractive because of the significant price difference between propane and propylene.

There are few references reported in the literature relating to the production of acrylic acid from propane. U.S. Pat. No. 5,198,580 discloses a process for partial oxidation of propane to yield acrylic acid, propylene, acrolein, acetic acid and carbon oxides by the reaction of propane in admixture with a molecular oxygen-containing gas in a reaction zone with a catalyst containing $Bi_bMo_cV_vA_aD_dE_eO_x$; where A is one or more of K, Na, Li, Cs and Tl; D is one or more of Fe, Ni, Co, Zn, Ce and La; E is one or more of W, Nb, Sb, Sn, P, Cu, Pb, B, Mg, Ca and Sr; values for a, d and e are from 0 to 10, b is from 0.1 to 10, c is from 0.1 to 20, v is from 0.1 to 10, c:b is from 2:1 to 30:1 and v:b is from 1:5 to 1 to 8. The acrylic acid yield achieved using the bismuth molybdate type of catalyst is 5.4% at 19% conversion of propane at a pressure of 20 psig and a temperature of 400° C.

European patent EP 0 608 838 A2 to Takashi et al. discloses a method of producing an unsaturated carboxylic acid, mostly in the explosive regime of the propane, air and water mixture at 380° C. in the presence of a catalyst containing a mixed metal oxide of MoVTeXO, wherein X is at least one element selected from bismuth, cerium, indium, tantalum, tungsten, titanium, zirconium, chromium, manganese, iron, ruthenium, cobalt, rhodium, nickel, palladium, platinum and antimony, wherein the proportion of the respective essential components are based on the total amount of the essential components exclusive of oxygen and satisfy the following formulae: $0.25<V_{Mo}<0.98$, $0.003<V_v<0.5$, $0.003<V_x<0.5$, wherein $V_{Mo}$, $V_v$, $V_{Te}$ and $V_x$ are molar fractions of Mo, V, Te and X.

Recently, Takashi et al. disclosed in another JP Patent No. 10 45 643 [98 45 643—Feb. 1998] the formation of acrylic acid and acrolein in the presence of $P_aMo_bV_cW_dX_eO_n$ (X=Nb, Ta, Ti, Zr, Sb; if a=1 then b=1–18, c=0–4, d=0–4 and e=0.05–20) at 380° C. achieving a yield 0.9% to acrolein and 3.5% to acrylic acid at 12% propane conversion.

The above-referenced catalysts disclosed in the literature result in low yields of acrylic acid at relatively high temperatures and produce propylene as one of the significant by-products. Propylene can be expensive to separate, especially in a recycling mode of operation.

Thus, none of the prior art discloses or suggests catalysts which provide for the selective production of acrylic acid and acrolein at low temperatures through a gas phase partial oxidation process of propane.

It would be desirable to provide a catalyst designed in such a way that a single catalyst selectively produces acrylic acid and acrolein from propane without the significant production of intermediates such as propylene.

OBJECTS OF THE INVENTION

It is an object of the invention to overcome the above-identified deficiencies.

It is another object of the invention to provide an improved catalytic system for the catalytic oxidation of propane to acrylic acid.

It is a further object of the invention to provide an improved catalyst system for the single stage oxidation of propane to acrylic acid.

It is a still further object of the invention to provide methods of making and using the improved catalytic system.

The foregoing and other objects and advantages of the invention will be set forth in or be apparent from the following description.

SUMMARY OF THE INVENTION

The invention relates to an improved catalyst system for the selective oxidation of propane and methods of making and using the same. According to one preferred embodiment of the invention, propane is selectively oxidized with molecular oxygen to acrylic acid and acrolein in a gas phase reaction at temperatures of 150° C. to 450° C. and at pressures from 1–50 bar. This is achieved using a novel catalyst with a calcined composition of $Mo_aV_bGa_cPd_dNb_eX_f$ wherein:

X=at least one element selected from the group consisting of La, Te, Ge, Zn, Si, In and W;

a is 1;

b is 0.01 to 0.9;

c is >0 to 0.2;

d is 0.0000001 to 0.2;

e is >0 to 0.2; and f is >0 to 0.5.

The numerical values of a, b, c, d, e and f represent the relative gram-atom ratios of the elements Mo, V, Ga, Pd, Nb and X, respectively, in the catalyst. The elements are preferably present in combination with oxygen in the form of various oxides.

The improved catalyst system is preferably prepared by the procedures disclosed in the examples.

Furthermore, this invention also relates to a selective low temperature catalytic process for the production of acrylic acid or acrolein or both by the vapor phase oxidation of propane, preferably in the non-explosive regime.

Other objects as well as aspects, features and advantages of the present invention will become apparent from a study of the present specification, including the claims and specific examples.

BRIEF DESCRIPTION OF THE FIGURES

FIG. 1 is an XRD pattern of a catalyst according to one embodiment of the invention.

FIG. 2 is an XRD pattern of a comparative catalyst.

DESCRIPTION OF THE PREFERRED EMBODIMENTS

One aspect of the invention relates to an improved catalytic system for the selective oxidation of propane. The catalytic system preferably comprises a calcined composition of $Mo_aV_bGa_cPd_dNb_eX_f$ wherein:

X=at least one element selected from the group consisting of La, Te, Ge, Zn, Si, In and W;

a is 1;

b is 0.01 to 0.9;

c is >0 to 0.2;

d is 0.0000001 to 0.2;

e is >0 to 0.2; and f is >0 to 0.5.

According to one embodiment of the invention, the catalyst composition comprises $Mo_aV_bGa_cPd_dNb_eX_fO_y$, wherein y is a number determined by the valence requirements of the other elements in the catalyst composition. The catalyst of the invention can be used with or without a support. Suitable supports for the catalyst include alumina, silica, titania, zirconia, zeolites, silicon carbide, Mo carbide, molecular sieves and other micro/nonporous materials, and mixtures thereof. When used with a support, the supported catalyst usually comprises from about 10 to 50% by weight of the catalyst composition, with the remainder being the support material.

Another aspect of the invention relates to methods of making the improved catalysts. The choice of the compounds used as well as the specific procedures followed in preparing a catalyst can have a significant effect on the performance of a catalyst. The elements of the catalyst composition are preferably in combination with oxygen as oxides.

Preferably, the catalyst is prepared from a solution of soluble compounds (salts, complexes or other compounds) of each of the metals. The solution is preferably an aqueous system having a pH of 1 to 10 and more preferably a pH of 1 to 7, at a temperature of from about 30 to about 100° C.

Generally, a mixture of compounds containing the elements is prepared by dissolving sufficient quantities of soluble compounds and dispersing the insoluble compounds so as to provide the desired gram-atom ratios of the elements in the catalyst composition. The catalyst composition is then prepared by removing the water and/or other solvent from the mixture of the compounds in the solution system. The dried catalyst is calcined by heating to a temperature from about 250° C. to about 450° C. in air or oxygen for a period of time from about one hour to about 16 hours to produce the desired catalyst composition.

Preferably, the molybdenum is introduced into the solution in the form of ammonium salts such as ammonium paramolybdate, or as organic acid salts of molybdenum such as acetates, oxalates, mandelates, and glycolates. Other partially water soluble molybdenum compounds which may be used include molybdenum oxides, molybdic acid, and chlorides of molybdenum.

Preferably, the vanadium is introduced into the solution in the form of ammonium salts such as ammonium metavanadate and ammonium decavanadate, or as organic salts of vanadium such as acetates, oxalates, and tartrates. Partially water soluble vanadium compounds such as vanadium oxides, and sulfates of vanadium can also be used. To achieve a complete solubility, a certain amount of oxalic or tartaric acid can be added.

Preferably, the gallium is introduced into the catalyst slurry in the form of salts of gallium such as oxide, chloride, nitrate, and the like.

Preferably, the palladium is introduced into the catalyst slurry in the form of Pd on activated charcoal or alumina or as a solution of salts of palladium such as acetates, chlorides, nitrates, and the like.

Preferably, the other metals are introduced into catalyst slurry in the form of salts of oxides, acetates, chlorides, nitrates, or the like.

Preferably, the niobium is used in the form of oxalates or hydrate oxides. Other sources of this metal in soluble form include compounds in which the metal is coordinated, bonded or complexed to a beta-diketonate, carboxylic acid, an amine, an alcohol, or an alkanolamine.

According to one preferred embodiment, the catalyst is prepared by the following general procedure. Aqueous solutions of vanadium and molybdenum are prepared separately. The vanadium solution is mixed with the molybdenum solution at a specified temperature and pH. The remaining required components are slowly added to the combined gel solution. After mixing, the resultant gel is dried to incipient wetness with continuous stirring.

After drying the resultant gel mixture at 120° C. for 16 hours, the resultant catalyst is heated to about 350° C. at a rate of 2° C. per minute and calcined at this temperature in air for 4 hours to produce the desired oxide composition.

Another aspect of the invention relates to a method of using the inventive catalyst system for the selective oxidation of propane to the acrylic acid.

The raw material used as the source of the propane can be a gas stream which contains at least three volume percent of propane or a mixture of propylene/propane. The gas stream can also contain some amounts of the $C_2$ or $C_4$ alkane and alkenes, preferably less than thirty volume percent of each. The gas stream can also contain major amounts, more than five volume percent, of diluents such as nitrogen/argon, carbon dioxide, and water in the form of steam.

In carrying out the process, the reaction mixture generally contains one mole of propane, 0.01 to 2.0 moles of molecular oxygen either as pure oxygen or in the form of air, and zero to 4.0 moles of water in the form of steam.

Molecular oxygen sources for the feed include purified oxygen, air and oxygen-enriched air, depending on the economics of separation and the hydrocarbon conversion achieved. The ratio of propane to oxygen varies with the desired conversion and the selectivity of the catalyst, but generally is in the range of 1/5–5/1.

The oxygen concentration in the feed gas mixture can vary widely, from 0.1 to 50% or higher of the feed mixture by applying proper measures to avoid explosion problems. Air is the preferred source of oxygen in the feed. The amount of oxygen present may be a stoichiometric amount, or lower, of the hydrocarbons in the feed.

The reaction can also be affected especially in the presence of diluents such as argon, nitrogen or steam. The ratio of propane to diluents can be in the range of 1/5–1/1.

The water vapor or steam may be used as a reaction diluent and as a heat moderator for the reaction. It also can act as a desorption accelerator of the reaction product in the vapor phase oxidation reaction. Other gases may be used as reaction diluents or heat moderators such as helium, nitrogen and carbon dioxide.

The liquid products of the reaction can be separated from the unreacted feed hydrocarbons by condensation or scrubbing, usually by water or dilute acid.

The gaseous components of the reaction mixture preferably include propane, oxygen or oxygen and diluents, and these components are preferably uniformly admixed prior to being introduced into the reaction zone. The components may be preheated, individually or after being admixed, prior to being introduced into the reaction zone which should have a temperature of from about 150° C. to about 450° C.

The reaction zone generally has a pressure of from 1 to 50 bar, preferably from 1 to 30 bar; a temperature of from about 150° C. to about 450° C., preferably from 200 to 300° C.; a contact time between the reaction mixture and the catalyst of from about 0.01 second to 100 seconds, preferably from 0.1 second to 10 seconds; and a space hourly velocity of from about 50 to about 50,000 h$^{-1}$, preferably from 100 to 10,000 h$^{-1}$ and most preferably from 200 to 3,000 h$^{-1}$.

The contact time is defined as the ratio between the apparent volume of the catalyst bed and the volume of the gaseous reaction mixture feed to the catalyst bed under the given reaction conditions in a unit of time.

The space velocity is calculated by determining the total reactor outlet gas equivalent in liters of the total effluent evolved over a period of one hour divided by the liters of catalyst in the reactor. This room temperature volume is converted to the volume at 0° C. at 1 bar.

The reaction pressure may be initially provided by the feed of the gaseous reactant and diluent and after the reaction has commenced, may be maintained by the use of a suitable back-pressure controller placed on the reactor outlet stream.

The reaction temperature is provided by placing the catalyst bed within a tubular converter having walls placed in a furnace heated to the desired reaction temperature.

One surprising advantage of the catalyst systems of the invention is the higher yields of acrylic acid achieved. Preferably, the oxidation can provide at least a 30% yield of acrylic acid.

The oxidation performed according to the invention preferably provides a selectivity to acrylic acid of at least 50% per single pass through the reaction zone, more preferably at least 70%.

Preferably, less than 1% propylene is formed using the catalyst system. More preferably, no detectable propylene is formed as a by-product.

The process is generally carried out in a single stage with all the oxygen and reactants being supplied as a single feed with non-reacted initial reactants being recycled. However, multiple stage addition of oxygen or hydrocarbon to the reactor can be used and/or recycling of un-reacted gases with purge mode can be applied to improve the overall productivity and/or yield of the desired products.

The methods of using the catalyst of the invention are not limited to the oxidation of propane to acrylic acid and acrolein. The catalyst may also be used for oxidizing n/iso C4, C5 in the vapor phase with molecular oxygen to produce the corresponding alpha-beta unsaturated carboxylic acids.

EXAMPLES

The following examples are illustrative of some of the products and methods of making the same falling within the scope of the present invention. They are, of course, not to be considered in any way limitative of the invention. Numerous changes and modifications can be made with respect to the invention.

The catalyst samples prepared in the examples were evaluated by using the following method.

Catalyst Testing:

Catalyst evaluations were carried out in a stainless steel fixed bed tubular reactor under standard process conditions. The gas feed compositions used for the evaluation of the catalysts contained propane, oxygen and nitrogen. Reactions were carried out at a temperature of 300° C., pressure of 15 psig and at space velocity of about 1,090 h$^{-1}$.

Reaction products were analyzed on-line by gas chromatography. Oxygen, argon and carbon monoxide were analyzed using a 2.5 m by 3 mm column of 13X molecular sieve. Carbon dioxide, propane and propylene were analyzed using a 2 m by 3 mm column packed with material sold under the trade name HAYESEP Q®. Liquids products (acrylic acid, acrolein, acetic acid and water) were collected for a certain period in the cold trap and were analyzed using a 2 m by 3 mm column packed with material sold under the trademark PORAPAK Q®. In all cases, the conversion and selectivity calculations were based on the reaction stoichiometry.

Example 1:
$$[Mo_1V_{0.398}Ga_{1.0E-05}Pd_{1.90E-04}Nb_{0.125}Te_{0.23}]$$

Ammonium metavanadate (Aldrich Chemicals, Assay= 99.0%) in the amount of 7.6 grams was added to 80 ml of distilled water and heated to 90° C. with stirring. 3.4 grams of niobium oxide (80% Nb$_2$O$_5$), 28 grams of oxalic acid, and 28.8 g ammonium paramolybdate tetra hydrated (Aldrich Chemicals A.C.S.-12054-85-2) were added to the vanadate solution to make a gel mixture. The required amount of palladium followed by telluric acid and gallium oxide were added slowly to gel mixture. The gel mixture was stirred vigorously to achieve a homogeneous gel mixture which was then dried slowly to incipient dryness with continuous stirring.

The resulting solid was put in a China dish and dried additionally in an oven at 120° C. The dried material was cooled to room temperature and placed in a furnace where the catalyst is calcined at 350° C. for 4 to 16 hours. The temperature was raised from room temperature to 350° C. at the rate of 20°/min and thereafter held at 350° C. for four hours.

The calcined catalyst was formulated into uniform particles of the 40–60 mesh size and evaluated for the propane oxidation reaction. The catalyst was evaluated at a temperature of 300° C. using a feed mixture containing propane:oxygen:nitrogen (20:10:70). The reaction product showed the following results:

Propane Conversion (%): 26.45

Acrylic acid sel. (%): 31

Acrolein sel. (%): 1

Acetic acid sel. (%): 21

CO$_x$ sel. (%): 47

The overall reaction products showed 53% oxygenated product and 47% total oxidation product.

Example 2:
$$[Mo_1V_{0.398}Ga_{1.0E-05}Pd_{1.90E-04}Nb_{0.125}Te_{0.23}La_{1.0E-05}]$$

The procedure was the same as Example 1 except the required amount of lanthanum nitrate was also added in the last step of preparation.

The calcined catalyst was formulated into uniform particles of the 40–60 mesh size and evaluated for the propane oxidation reaction. The catalyst was evaluated at a temperature of 300° C. using a feed mixture containing propane:oxygen:nitrogen (20:10:70). The reaction product showed the following results:

Propane Conversion (%): 21.21

Acrylic acid sel. (%): 21

Acrolein sel. (%): 1

Acetic acid sel. (%): 13

CO$_x$ sel. (%): 65

The overall reaction products showed 35% oxygenated product and 65% total oxidation product.

Example 3:
$$[Mo_1V_{0.398}Ga_{1.0E-05}Pd_{1.90E-04}Nb_{0.125}Te_{0.23}Zn_{1.0E-05}]$$

The procedure was same as described in Example 1 except the required amounts of zinc nitrate and telluric acid were also added in the last step of preparation. The calcined catalyst was formulated into uniform particles of the 40–60 mesh size and evaluated for the propane oxidation reaction. The catalyst was evaluated at a temperature of 300° C. using a feed mixture containing propane:oxygen:nitrogen (20:10:70). The reaction product showed the following results:

Propane Conversion (%): 20
Oxygen Conversion (%): 100
Acrylic acid sel. (%): 26
Acrolein sel. (%): 1
Acetic acid sel. (%): 15
$CO_x$ sel. (%) 58

The overall reaction products showed 42% oxygenated product and 58% total oxidation product.

Example 4:

$[Mo_1V_{0.398}Ga_{1.0E-05}Pd_{1.90E-04}Nb_{0.125}Te_{0.23}]$

The catalyst is same as described in Example 1. The calcined catalyst was formulated into uniform particles of the 40–60 mesh size and was evaluated at a temperature of 300° C. using a feed mixture containing propane:oxygen (95.25:4.75). The reaction product showed the following results:

Propane Conversion (%): 4.22
Oxygen Conversion (%): 100
Acrylic acid sel. (%): 45.5
Acrolein sel. (%): 5.5
Acetic acid sel. (%): 12
$CO_x$ sel. (%): 37

The overall reaction products showed 63% oxygenated product and 37% total oxidation product.

Example 5:

$[Mo_1V_{0.398}Ga_{1.0E-05}Pd_{1.90E-04}Nb_{0.125}Te_{0.23}]$

The catalyst used for this example is same as in Example 1. The calcined catalyst was formulated into uniform particles of the 40–60 mesh size and evaluated for the propane oxidation reaction. The catalyst was evaluated at a temperature of 300° C. using a feed mixture containing propane:oxygen (90:10). The reaction products showed the following results:

Propane Conversion (%): 9
Oxygen Conversion (%): 100
Acrylic acid sel. (%): 35.5
Acrolein sel. (%): 3.5
Acetic acid sel. (%): 10
$CO_x$ sel. (%): 51

The overall reaction products showed 49% oxygenated product and 51% total oxidation product.

Example 6:

$[Mo_1V_{0.398}Ga_{1.0E-05}Pd_{1.15E-04}Nb_{0.125}Te_{0.30}]$

The procedure for the preparation of the catalyst is same as described in Example 1 except different amounts Pd and tellurium were added. The calcined catalyst was formulated into uniform particles of the 40–60 mesh size and evaluated for the propane oxidation reaction. The catalyst was evaluated at a temperature of 300° C. using a feed mixture containing propane:oxygen:nitrogen (20:10:70). The reaction products showed the following results:

Propane Conversion (%): 17.14
Oxygen Conversion (%): 100
Acrylic acid sel. (%): 13
Acrolein sel. (%): 1
Acetic acid sel. (%): 10
$CO_x$ sel. (%): 76

The overall reaction products showed 24% oxygenated product and 76% total oxidation product.

The BET surface area for the catalysts described in above Examples 1–6 varied from 20 to 35 $m^2/g$.

An XRD pattern for a catalyst according to one embodiment of the invention is shown in FIG. 1. The catalysts disclosed in the present invention preferably have a structure which produces diffused or poorly crystallized patterns with a strong reflection peak at 22 (4.00° Å) and a very broad peak at 27 (3.57 Å) two theta values. Generally, to obtain this structure, a catalyst has to be prepared by the methods described above. The very broad peak at 3.57 Å is a kind of diffused peak and is difficult to attribute to any one phase. However, when these types of catalysts are calcined at higher temperatures other well defined reflections appear and these are not active for the activation of alkanes to oxygenated products, as shown in Example No. 7 (below).

The catalysts of the present invention showed an optimum redox behavior resulting a high activity and high selectivity towards the partial oxidation products. Based on catalytic data, the following general characteristics can be concluded for the catalysts disclosed in the present application.

1. The catalysts show high selectively to acrylic acid at low temperature.

2. The oxidation of propane shows lower ΔT of 10–15° C. Lower ΔT can have a positive impact on the reactor design.

3. Relative selectivity to oxygenated products (acrylic acid, acrolein and acetic acid) depends on the catalyst composition, reaction temperature, space velocity, pressure and feed composition (alkane, oxygen, steam, nitrogen).

Comparative Example 7: $[Mo_1V_{0.39}Nb_{0.125}Te_{0.23}]$

The catalyst composition and procedure were the same as described in EP patent publication no. 0 608 838 for comparative purposes. The catalyst was calcined at 600° C. as described in the EP patent publication. The XRD pattern of the catalyst, FIG. 2, shows all well defined reflections at 22.1, 28.2, 36.2, 45.2 and 50 at two theta values, as described in the EP patent publication. The calcined catalyst was formulated into uniform particles of the 40–60 mesh size and evaluated for the propane oxidation reaction at temperatures of 300 and 380° C. with a feed mixture containing propane:oxygen:nitrogen (20:10:70). The catalyst was not active at both temperatures.

The above description of the invention is intended to be illustrative and not limiting. Various changes or modifications in the embodiments described may occur to those skilled in the art. These can be made without departing from the spirit or scope of the invention.

What is claimed is:

1. A catalyst system for selective oxidation of propane to oxygenated products including acrylic acid, acrolein and acetic acid, said catalyst system containing a catalyst composition comprising $Mo_aV_bGa_cPd_dNb_eX_fO_y$ wherein
X=at least one element selected from La, Te, Ge, Zn, Si, In and W;
a is 1;
b is 0.01 to 0.9;
c is >0 to 0.2;
d is 0.0000001 to 0.2;
e is >0 to 0.2;
f is >0 to 0.5; and
y is a number determined by the valence requirements of the elements in the catalyst composition,
wherein the numerical values of a, b, c, d, e, f, and y represent the relative gram-atom ratios of the elements Mo, V, Ga, Pd, Nb, X and O, respectively, in the catalyst composition.

2. A catalyst system for selective oxidation of propane to oxygenated products including acrylic acid, acrolein and acetic acid, said catalyst system comprising a Mo-V-Ga-Pd-Nb-X-O catalyst composition made by a process comprising the steps of:
(a) combining the elements Mo, V, Ga, Pd, Nb and X to form a mixture in the following ratio: $Mo_aV_bGa_cPd_dNb_eX_f$, wherein:
X=at least one element selected from La, Te, Ge, Zn, Si, In and W;
a is 1;
b is 0.01 to 0.9;
c is >0 to 0.2;
d is 0.0000001 to 0.2;
e is >0 to 0.2; and
f is >0 to 0.5; and
b) calcining said mixture thereby incorporating oxygen to form said catalyst composition.

3. The catalyst system according to claim 1, wherein the catalyst composition exhibits two X-rays diffraction peaks at the following two theta values: a strong peak at 22 (+0.3) and a very broad peak at 27 (+0.5).

4. The catalyst of claim 1, wherein said catalyst is a supported catalyst system comprising a support.

5. The catalyst of system claim 2, wherein said catalyst is a supported catalyst comprising a support.

6. The catalyst system of claim 4, wherein said support is selected from the group consisting of alumina, silica, titania, zirconia, silicon carbide, Mo-carbide, zeolites, and molecular sieves.

7. The catalyst of system claim 4, wherein said supported catalyst comprises from greater than 0 to 50% by weight catalyst composition and 50 to 95% by weight support.

8. A process of forming the catalyst composition of claim 1, comprising the steps of:
a) forming a mixture containing the elements Mo, V, Ga, Pd, Nb, and X in solution;
b) drying said mixture to form a dried solid material; and
c) calcining said dried solid material to form said catalyst composition.

9. The process of claim 8, wherein said calcining comprises heating said dried solid material to a calcining temperature from about 250 to 450° C. in air or oxygen for period of time from about one hour to about 16 hours.

10. A catalyst system for selective oxidation of propane to oxygenated products including acrylic acid, acrolein and acetic acid, said catalyst system containing a catalyst composition comprising $Mo_aV_bGa_cPd_dNb_eX_fO_y$
wherein
X=at least one element selected from La, Te, Ge, Zn, Si, In and W;
a is 1;
b is 0.01 to 0.9;
c is >0 to 0.2;
d is 0.0000001 to 0.2;
e is >0 to 0.2; and
f is >0 to 0.5; and
y is a number determined by the valence requirements of the elements in the catalyst composition,
wherein the numerical values of a, b, c, d, e, f, and y represent the relative gram-atom ratios of the elements Mo, V, Ga, Pd, Nb, X and O, respectively, in the catalyst composition,
and wherein said catalyst composition is made by a process comprising the steps of:
(a) combining the elements Mo, V, Ga, Pd, Nb and X to form a mixture; and
(b) calcining said mixture thereby incorporating oxygen to form said catalyst composition.

11. The catalyst system of claim 10, wherein the catalyst composition exhibits two X-rays diffraction peaks at the following two theta values: a strong peak at 22 (+0.3) and a very broad peak at 27 (+0.5).

12. The catalyst system of claim 10, wherein said catalyst system is a supported catalyst comprising a support.

13. The catalyst system of claim 12, wherein said support is selected from the group consisting of alumina, silica, titania, zirconia, silicon carbide, Mo-carbide, zeolites, and molecular sieves.

14. The catalyst system of claim 12, wherein said supported catalyst comprises from greater than 0 to 50% by weight catalyst composition and 50 to 95% by weight support.

15. The catalyst system of claim 2, wherein the catalyst composition exhibits two X-rays diffraction peaks at the following two theta values: a strong peak at 22 (+0.3) and a very broad peak at 27 (+0.5).

16. The catalyst system of claim 5, wherein said support is selected from the group consisting of alumina, silica, titania, zirconia, silicon carbide, Mo-carbide, zeolites, and molecular sieves.

17. The catalyst system of claim 5, wherein said supported catalyst comprises from greater than 0 to 50% by weight catalyst composition and 50 to 95% by weight support.

18. The catalyst system of claim 4, wherein said support is selected from the group consisting of microporous materials and nanoporous materials.

19. The catalyst system of claim 5, wherein said support is selected from the group consisting of microporous materials and nanoporous materials.

20. The catalyst system of claim 12, wherein said support is selected from the group consisting of microporous materials and nanoporous materials.

21. The process of claim 8, wherein said mixture is a solution of soluble compounds of each of the elements.

22. The catalyst system of claim 2, wherein said mixture is a solution of soluble compounds of each of the elements.

23. The process of claim 21, wherein the solution is an aqueous solution having a pH of 1 to 10.

24. The process of claim 21, wherein the solution is an aqueous solution having a pH of 1 to 7.

25. The catalyst of claim 2, wherein said calcining is at a temperature from about 250° C. to about 450° C.

26. A process of forming the catalyst composition of claim 1, comprising the steps of:
a) forming a mixture containing the elements Mo, V, Ga, Pd, Nb, and X in solution; and
b) calcining to form said catalyst composition.

27. The catalyst system of claim 3, wherein said catalyst system is a supported catalyst comprising a support.

28. The catalyst system of claim 27, wherein said supported catalyst comprises from greater than 0 to 50% by weight catalyst composition and 50 to 95% by weight support.

29. A process of forming the catalyst composition of claim 1, comprising the steps of:
a) forming a mixture consisting essentially of the elements Mo, V, Ga, Pd, Nb, and X in solution; and
b) calcining to form said catalyst composition.

* * * * *